(12) United States Patent
Curry et al.

(10) Patent No.: US 8,123,772 B2
(45) Date of Patent: Feb. 28, 2012

(54) CAP FOR LANCING DEVICE WITH ADJUSTABLE MODE OF OPERATION

(75) Inventors: Samuel Mason Curry, Oakland, CA (US); Jonathan M. Wyler, Boston, MA (US)

(73) Assignee: Abbott Diabetes Care Inc., Alameda, CA (US)

( * ) Notice: Subject to any disclaimer, the term of this patent is extended or adjusted under 35 U.S.C. 154(b) by 409 days.

(21) Appl. No.: 12/191,737

(22) Filed: Aug. 14, 2008

(65) Prior Publication Data

US 2010/0042128 A1 Feb. 18, 2010

(51) Int. Cl.
*A61B 17/14* (2006.01)

(52) U.S. Cl. ...................................... 606/181

(58) Field of Classification Search .................. 606/181, 606/182, 183, 172; 600/566, 567, 583; 604/136–139
See application file for complete search history.

(56) References Cited

U.S. PATENT DOCUMENTS

| | | | |
|---|---|---|---|
| 4,375,815 A | 3/1983 | Burns | |
| 4,462,405 A | 7/1984 | Ehrlich | |
| 4,637,403 A | 1/1987 | Garcia et al. | |
| 4,990,154 A | 2/1991 | Brown et al. | |
| 5,423,847 A | 6/1995 | Strong et al. | |
| 5,540,709 A | 7/1996 | Ramel | |
| 5,613,978 A | 3/1997 | Harding | |
| 5,628,764 A | 5/1997 | Schraga | |
| 5,628,765 A * | 5/1997 | Morita | 606/182 |
| 5,666,966 A | 9/1997 | Horie et al. | |
| 5,857,983 A | 1/1999 | Douglas et al. | |
| 5,873,887 A | 2/1999 | King et al. | |
| 5,879,311 A | 3/1999 | Duchon et al. | |
| 5,879,367 A | 3/1999 | Latterell et al. | |
| 5,951,492 A | 9/1999 | Douglas et al. | |
| 5,951,493 A | 9/1999 | Douglas et al. | |
| 5,964,718 A | 10/1999 | Duchon et al. | |
| 6,056,701 A | 5/2000 | Duchon et al. | |
| 6,066,103 A | 5/2000 | Duchon et al. | |
| 6,071,250 A | 6/2000 | Douglas et al. | |

(Continued)

FOREIGN PATENT DOCUMENTS

WO WO2005046477 5/2005

OTHER PUBLICATIONS

PCT International Search Report (Date of Mailing: Nov. 2, 2009); PCT/US2009/053644, filed Aug. 13, 2009.

*Primary Examiner* — Ryan Severson
*Assistant Examiner* — Jonathan W Miles
(74) *Attorney, Agent, or Firm* — Young Basile (57) ABSTRACT

Caps and cap assemblies for lancing devices with adjustable modes of use are disclosed herein. In accordance with some embodiments of the invention, an adjustable cap assembly for a lancing device having a housing is disclosed. The assembly comprises at least one cap comprising a cap body with a skin-engaging end that defines a piercing aperture, an end opposite the skin-engaging end configured to removably engage an end of the housing and a lancet receiver within the cap body and configured to receive a lancet. The at least one cap is configured to adjust a penetration depth of the lancet with axial movement of the cap relative to the housing and to adjust an effective size of the piercing aperture with the lancet receiver.

8 Claims, 6 Drawing Sheets

U.S. PATENT DOCUMENTS

| | | |
|---|---|---|
| 6,086,545 A | 7/2000 | Roe et al. |
| 6,156,050 A | 12/2000 | Davis et al. |
| 6,210,420 B1 | 4/2001 | Mauze et al. |
| 6,319,210 B1 | 11/2001 | Douglas et al. |
| 6,332,871 B1 | 12/2001 | Douglas et al. |
| 6,464,649 B1 | 10/2002 | Duchon et al. |
| 6,491,709 B2 | 12/2002 | Sharma et al. |
| 2002/0010406 A1 | 1/2002 | Douglas et al. |
| 2002/0022789 A1 | 2/2002 | Perez et al. |
| 2002/0029058 A1 | 3/2002 | Levaughn et al. |
| 2002/0082521 A1 | 6/2002 | Sharma et al. |
| 2002/0188223 A1 | 12/2002 | Perez et al. |
| 2003/0195540 A1 | 10/2003 | Moerman |
| 2004/0073140 A1 | 4/2004 | Douglas et al. |
| 2004/0162573 A1 | 8/2004 | Kheiri |
| 2004/0236251 A1 | 11/2004 | Roe et al. |
| 2004/0254599 A1 | 12/2004 | Lipoma et al. |
| 2005/0085839 A1 | 4/2005 | Allen et al. |
| 2005/0096686 A1 | 5/2005 | Allen |
| 2005/0215925 A1 | 9/2005 | Chan |
| 2006/0184189 A1 | 8/2006 | Olson et al. |
| 2006/0271084 A1 | 11/2006 | Schraga |
| 2006/0287664 A1 | 12/2006 | Grage, Jr. et al. |
| 2008/0027474 A1* | 1/2008 | Curry et al. .................. 606/181 |
| 2009/0043326 A1 | 2/2009 | Zhong |

* cited by examiner

CAP FOR LANCING DEVICE WITH ADJUSTABLE MODE OF OPERATION

BACKGROUND

Lancing devices are typically handheld units that permit users to draw blood for testing and diagnostic purposes. These devices include a housing with a piercing aperture, a lancet and a firing mechanism. The firing mechanism typically includes a spring or other biasing means which can be cocked either by insertion of the lancet or by pulling a cocking handle, for example. Once the lancing device is cocked, it is placed against the user's skin, often the fingertip. The user can then press a trigger to actuate the firing mechanism, which momentarily drives the sharp tip of lancet through the piercing aperture to puncture the user's skin and draw blood. When the lancing operation is complete, the user can press a second actuator to eject the lancet for removal and disposal. A consideration in the design of both lancets and lancet devices is to minimize parts and thus minimize cost of production.

Another consideration in the design of lancets is to minimize the discomfort experienced by users during the lancing process. To this end, some lancing devices include mechanisms to adjust the distance that the lancet sharp protrudes through the piercing aperture, thus regulating the depth that the lancet penetrates the user's skin. In some cases, these depth adjustment mechanisms include adjustable stops that limit the forward movement of the lancet during firing. In other cases, a lancet holder is moved axially within a lancing device housing to move the needle closer to or farther away from the piercing aperture, thus adjusting penetration depth.

Lancing devices can draw blood from a user's fingertip or other body part. A fingertip is a good testing site because it contains a large number of blood vessels and it is therefore easy to draw an adequate quantity of blood from the fingertip. However, fingertips are also sensitive and users who must frequently draw blood samples may experience discomfort from repeated sampling of the fingertips. Therefore, some users also perform lancing operations on parts of the body, and this is known as alternate site testing or alternate site incision, also known as "AST."

To effectively draw blood from an alternate site, it is helpful to have the needle penetrate the skin more deeply. It is also helpful to have a relatively wide piercing aperture. A wider piercing aperture acts as an expression ring by allowing the skin to pucker into the aperture's opening and by compressing a wider area of skin around the incision. When skin protrudes through the aperture into the housing, it is also more deeply penetrated by the lancet.

Another consideration in the design of lancing devices is to avoid accidental needle pricks when inserting and removing lancets from the lancing device. To this end, lancets include safety features such as frangible tabs which cover the needle sharp prior to insertion in the lancing device. Once the lancet is inserted, the use can break off and remove the frangible tab. Some lancets also include sleeves coaxially mounted to the main body of the lancet. The sleeve can be positioned so that it protectively encloses the needle sharp. During the lancing operation, the main body of the lancet slides through the sleeve to expose the lancet sharp. After removal of the lancet, however, the sleeve can be locked in its protective position, reducing the likelihood that a person handling the use lancet will prick himself or herself.

Another consideration in the design of lancing systems is the ease with which a lancet can be inserted into the lancing device. It is known that when a lancet is inserted into a lancing device, the force of the insertion can be used to cock the device. However, if the device is already cocked, and a lancet was to be inserted, there is some risk that the device would discharge during the insertion process and the user would be accidentally pricked. It is also known to insert the lancet into the lancet device when the cap of the device is removed.

SUMMARY

Caps and cap assemblies for lancing devices with adjustable modes of use are provided. In accordance with some embodiments of the invention, an adjustable cap assembly for a lancing device having a housing is disclosed. The assembly comprises at least one cap comprising a cap body with a skin-engaging end that defines a piercing aperture, an end opposite the skin-engaging end configured to removably engage an end of the housing and a lancet receiver within the cap body and configured to receive a lancet. The at least one cap is configured to adjust a penetration depth of the lancet with axial movement of the cap relative to the housing and to adjust an effective size of the piercing aperture with the lancet receiver.

In accordance with other embodiments of the invention, a cap assembly for a lancing device with a housing and a lancet firing mechanism disposed therein is disclosed. The cap assembly comprises a first cap and a second cap each having a lancet receiver. The first cap comprises a skin-engaging end defining a piercing aperture, an end opposite the skin-engaging end configured to removably attach to the housing and a lancet receiver configured to receive a lancet through the piercing aperture. The second cap comprises a skin-engaging end defining a peripheral skin engaging surface, an end opposite the skin-engaging end and configured to removably attach to the housing and a lancet receiver configured to receive the lancet and positioned within the second cap such that an end of the lancet receiver is circumscribed by and is substantially co-planar with the peripheral skin engaging surface, the receiver end defining the piercing aperture. The lancet, when in the lancet receiver of either cap, engages the lancet firing mechanism within the housing.

In accordance with yet other embodiments of the invention, a cap with adjustable modes for a lancing device having a housing is disclosed. The cap comprises a cap body with a skin-engaging end defining a piercing aperture, an end opposite the skin-engaging end configured to removably attach an end of the housing and a lancet receiver movably attached within the cap body and configured to receive a lancet. The lancet receiver has at least one protrusion extending through at least one opening in the cap body, and movement of the at least one protrusion moves the lancet receiver between a forward position in which an end of the lancet receiver is interposed in the piercing aperture and a rearward position distanced from the skin-engaging end of the body.

BRIEF DESCRIPTION OF THE DRAWINGS

The description herein makes reference to the accompanying drawings wherein like reference numerals refer to like parts throughout the several views, and wherein.

DETAILED DESCRIPTION OF THE EMBODIMENTS

Overview

Figure 1:
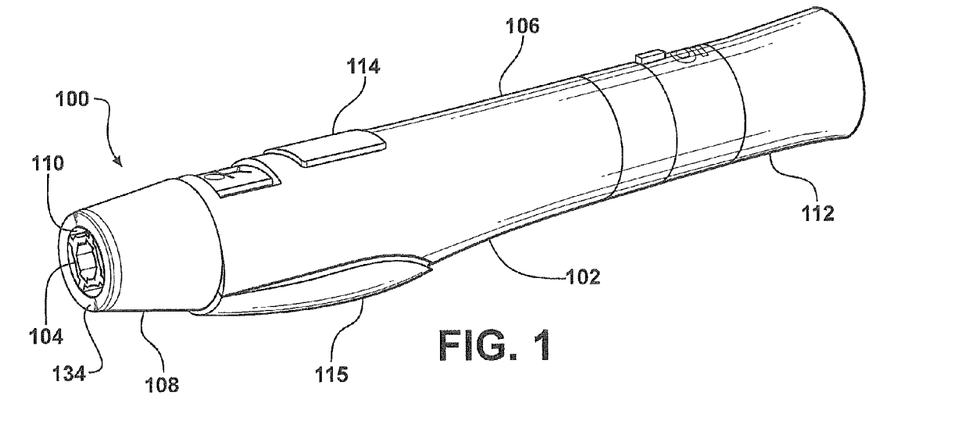
FIG. 1 is a perspective view of an example of a lancing device for use with the embodiments disclosed herein, including a removable lancet inserted therein.

Referring to FIG. 1, an example of a lancing system 100 is illustrated, including a lancing device 102 and removable lancet 104. The lancing system 100 is operated by a user to draw a sample of blood or other bodily fluid from the body such as for diagnostic purposes. The lancing device 102 includes a housing 106 with a skin-engaging cap 108 having a piercing aperture 110, a cocking handle 112 used to cock an internal firing mechanism, a trigger 114 for firing the internal firing mechanism, and an ejection slide 115 to eject the lancet 104 from the lancing device 102 after use.

Figure 2:
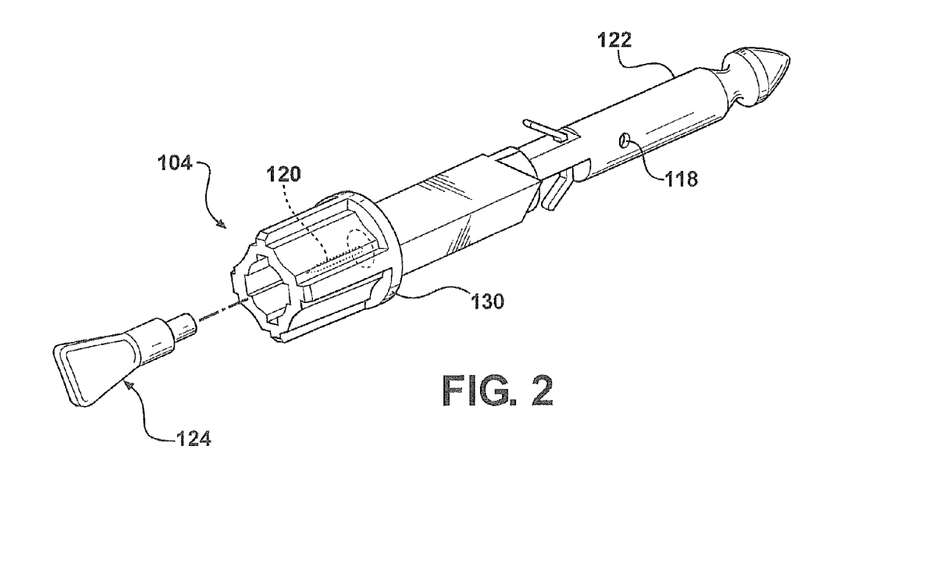
FIG. 2 is a perspective view of a lancet that can be used with the lancing device of FIG. 1, including a removable tab and a sleeve in an extended position to protectively surround the lancet's needle.

As shown in FIG. 2, the lancet 104 includes a needle 118 whose length (excluding a sharp tip 120) is encased in an elongated lancet body 122. A removable tab 124 can be frangibly attached to the front end of the lancet body 122. A sleeve 130 slides axially over a portion of the lancet body 122 between a forward position (as shown in FIG. 2), in which it protectively surrounds the sharp tip 120 of the needle 118, and a rearward position in which a portion of the sharp tip 120 protrudes beyond the front end of the sleeve 130.

The lancing system 100 can also be used in a kit which can include test strips and an analyzer. After the lancing system 100 is operated to draw blood, the user can apply the bead of blood to the test strip and insert the test strip into the analyzer for assessment of blood composition, such as levels of glucose.

Cap Embodiments

Figure 3:
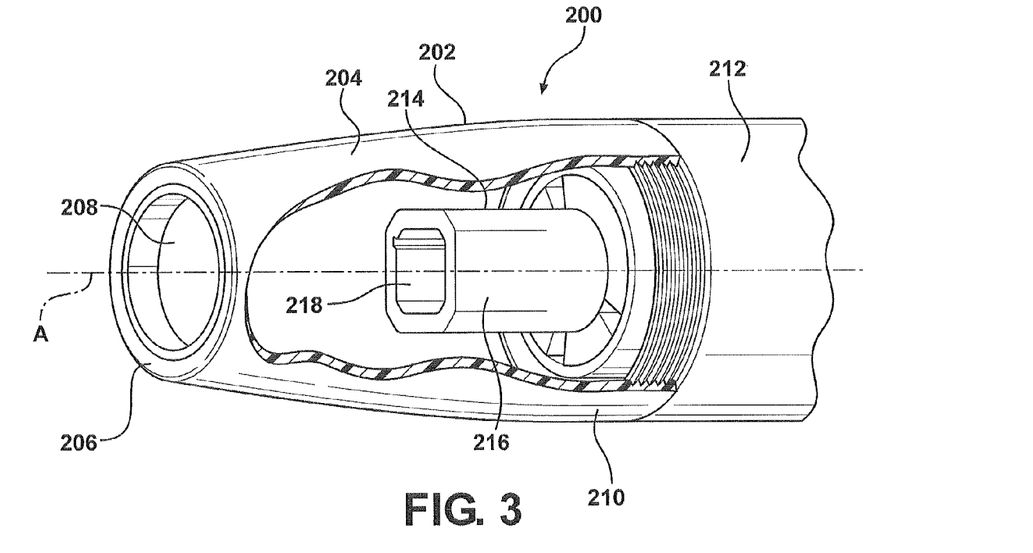
FIG. 3 is a perspective view of an embodiment of a cap assembly as disclosed herein.
Figure 4:
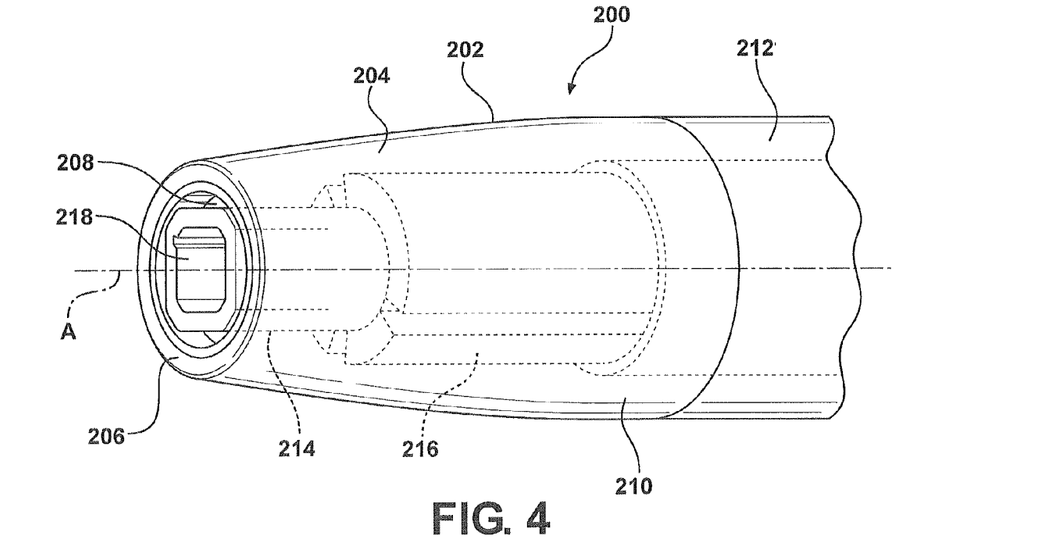
FIG. 4 is another perspective view of the embodiment of the cap assembly of FIG. 3.

In accordance with one embodiment of the invention, an adjustable cap assembly for a lancing device is illustrated in FIGS. 3 and 4. The assembly 200 comprises at least one cap 202 comprising a cap body 204 with a skin-engaging end 206 that defines a piercing aperture 208, an end 210 opposite the skin-engaging end configured to removably engage an end of a housing 212 of the lancing device, and a lancet receiver 214 within the cap body 204 and configured to receive a lancet (as seen in FIGS. 1 and 2). The at least one cap 202 is configured to adjust a penetration depth of the lancet with axial movement of the cap 202 relative to the housing 212 and to adjust an effective size of the piercing aperture 208 with the lancet receiver 214. Axial movement is defined as movement along axis A, as shown in FIGS. 3 and 4.

The cap 202 may be opaque (so that users do not see the sharp tip of the lancet), transparent, or colored and can provide protective closure around the lancet when the lancet is inserted into the lancet receiver 214. Although the cap 202 may be constructed in a variety of sizes and configurations, in certain embodiments the piercing aperture 208 may be about 3 mm to about 15 mm in diameter and the skin-engaging surface 206 may have a width of about 1 mm to about 3 mm. The skin-engaging surface 206 can be circular or can have other shapes and need not be continuous or completely annular. The skin-engaging surface 206 may form a compression ring.

Although referred to as a skin-engaging surface, such surface does not have to actually come in contact with a user's skin. As non-limiting examples, there may be an intervening cover on the skin-engaging surface such as a non-slip or sterility coating or film. A deformable ring may be incorporated to form a seal on the tissue. There can be protrusions for stimulation or blood expression.

The lancet is loaded into the lancet receiver 214 through piercing aperture 208 while the cap 202 is attached to the housing 212. The lancet receiver 214 releasably engages the lancet or the lancet sleeve if the lancet is of such a type. The lancet receiver 214 is generally tubular in construction with a receiver body 216 defining an elongated inner chamber 218 therein that is sized and configured to receive a lancet such as the one shown in FIG. 2. For example, the diameter of the lancet receiver 214 can range from 3 mm to less than 6 mm. The elongated interior chamber 218 is configured for mating engagement with the external contours of the lancet and/or lancet sleeve. When the lancet is fully inserted into the lancet receiver 214, an end of the lancet will engage with a lancet firing mechanism disposed within the housing that is configured to move the lancet between a cocked position and an extended position to lance the user's skin. Lancet firing mechanisms are known to those skilled in the art and will not be described in detail here.

As explained below, a single cap 202 can be used when the lancing device is operated in both finger mode and an alternate site test mode (hereinafter "AST mode"), or interchangeable caps can be used with the same lancing device to change between finger and AST modes. In AST mode, the cap 202 is configured for use with fleshy parts of the body such as a thigh or forearm. In finger mode, the cap 202 is configured for use with a fingertip.

Referring to FIG. 3, the cap 202 in an AST mode is shown. In AST mode, the lancet receiver 214 is positioned sufficiently spaced apart from the piercing aperture 208 to permit skin to pucker through the piercing aperture 208 during lancing when in the rearward position. The cap 202 is placed against a fleshy part of the body other than the fingertip. The skin-engaging end 206 engages the user's skin, causing it to pucker inside the relatively wide piercing aperture 208. The puckered flesh is then pierced by the lancet's sharp tip, allowing the user to apply pressure before, during and after lancing to help with blood acquisition. Clearance prevents wicking of the blood drop and allows the user to see when sufficient blood has been acquired. In other words, when the lancet receiver 214 is withdrawn from the piercing aperture 208, it adjusts the effective size of the piercing aperture 208 to a larger diameter—in this embodiment, the diameter of unobstructed piercing aperture 208. This larger diameter is sufficiently large to allow the user's skin to pucker into the piercing aperture 208.

Referring to FIG. 4, the cap 202 in a finger mode is shown. In finger mode, the lancet receiver 214 is slid toward the front end of the cap 202 (by means described below), so that the front end 216 of the lancet receiver 214 is interposed in or obstructs a portion of the piercing aperture 208, providing in conjunction with the skin-engaging surface 206, a skin-engaging contour that is suitable for placement against a finger. The obstruction of the piercing aperture 208 that is effected by the lancet receiver 214 need not be complete; rather the receiver 214 can be placed in proximity to the piercing aperture 208 so that the user's skin will encounter the receiver 214 when the cap 202 is placed against the user's body prior to firing the lancing device, and consequently, the user's skin will not be able to pucker into the cap 202 through piercing aperture 208, at least to the same extent as the skin could pucker if the lancet receiver 214 was not obstructing piercing aperture 208. When the lancet receiver 214 obstructs the piercing aperture 208, front end 216 of receiver 214 can be substantially coplanar with skin-engaging surface 206. In other words, when the lancet receiver 214 is interposed within the piercing aperture 208, it adjusts the effective size of the piercing aperture 208 to the smaller diameter of the front end 216 of the receiver 214.

The mode change between finger and AST is accomplished by axial movement of the lancet receiver 214 between the two positions. This movement can be achieved, for example, with a cam trail and cam follower, a lever moved in the direction along axis A, or a button that is pushed in or out between the positions. The lancet receiver 214 can be configured with one or more protrusions, such as arms or buttons, extending through the cap body that is pushed if one and squeezed if two to move the protrusion from one position to the other, with the lancet receiver 214 following. Other means of moving the lancet receiver known to those skilled in the art can be used as desired or required.

The cap 202 is configured to adjust a penetration depth of the lancet with axial movement of the cap 202 relative to the housing 212. As mentioned above, when the lancet is fully inserted into the lancet receiver 214, an end of the lancet will engage with a lancet firing mechanism disposed within the housing 212. Once engaged, the lancet is fixed relative to the housing 212. With the lancet fixed in relation to the housing 212, the depth to which the lancet will penetrate the skin can be adjusted by moving the cap 202 away from and toward the housing 212 along the axis A. This penetration depth adjustment can be performed in both the finger mode and the AST mode. The penetration depth of the lancet is at its maximum when the cap 202 is positioned closest to the housing 212 along the axis A. The penetration depth is at its minimum when the cap 202 is positioned farthest from the housing 212 along axis A. The depth of penetration can be adjusted based on the user's comfort, the amount of blood required, the thickness of the user's skin, and the like.

The cap 202 can be moved along the axis A in any way known by those skilled in the art. For example, the cap 202 and housing 212 can snap together at different depths, wherein squeezing the cap provides clearance to move between depths. The cap 202 can be moved with a cam trail and a cam follower. An intermediate member can be used between the cap 202 and the housing 212 with the cam trail and follower, or can be used in a telescoping manner. The cap 202 can friction fit the housing 212 and be pulled or pushed along the axis. The end 210 of the cap opposite the skin-engaging end 206 can be threaded, with the corresponding end of the housing 212 also threaded. The penetration depth can be adjusted by rotating the cap 202 on the housing 212. The motion of depth adjustment along the axis A can be limited by the length of the threads, cam or other adjustment means or alternatively stops can be incorporated to limit the length of movement.

The cap 202 can be removed from the housing 212 to permit cleaning of the interior of the cap 212 and the lancet receiver 214, as well as the interior of the lancing device. To permit its removal, the cap 108 can be threadably connected to housing 106 or connected via snap fit as discussed above. However, during operation of lancing device it is not necessary to remove cap 202 as the device is loaded with the lancet through the cap.

Alternatively, the assembly 200 can comprise two caps 202 identical in configuration as described above, with one cap having the lancet receiver 214 fixed in the finger mode position and the second cap having the lancet receiver 214 fixed in the AST mode position. The lancet receiver 214 can be fixedly disposed with in the caps or can be integral with the caps, i.e. molded from the same piece.

Figure 5A:
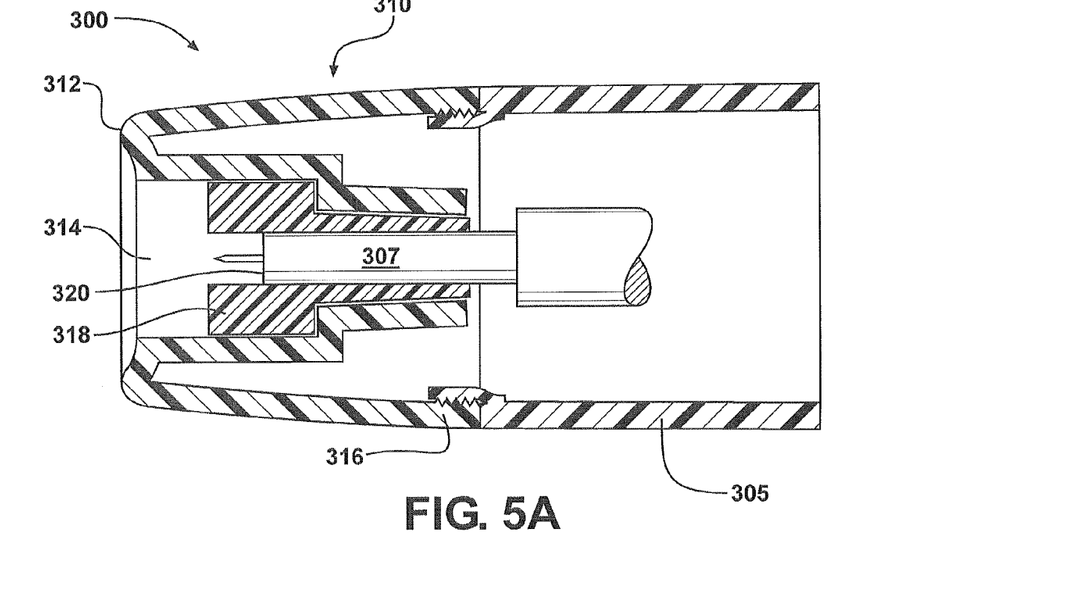
FIGS. 5A and 5B are cross sectional views of another embodiment of a cap assembly as disclosed herein.
Figure 5B:
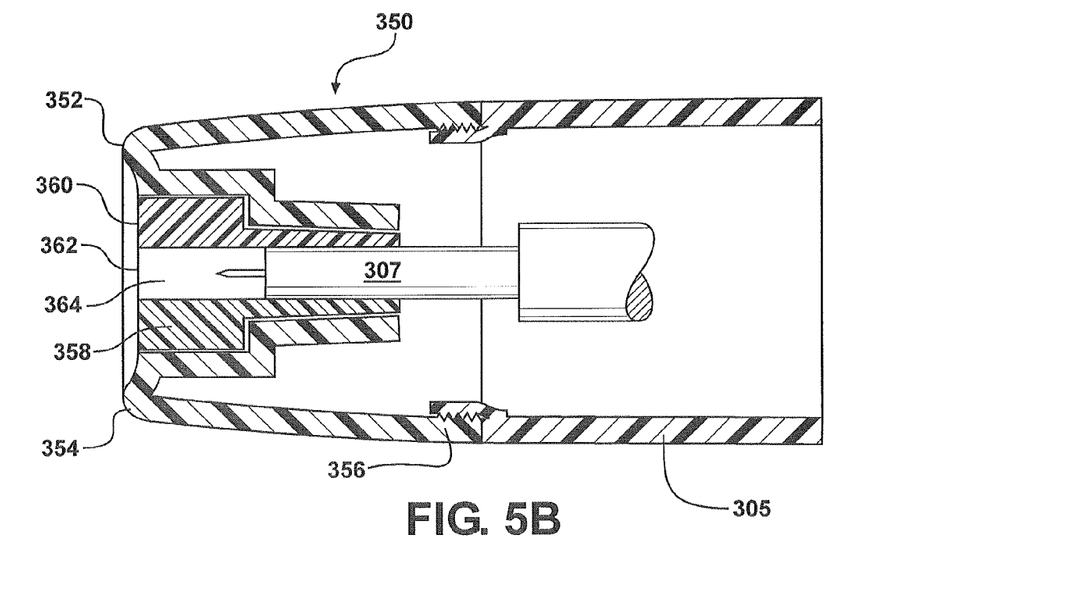
Figure 6:
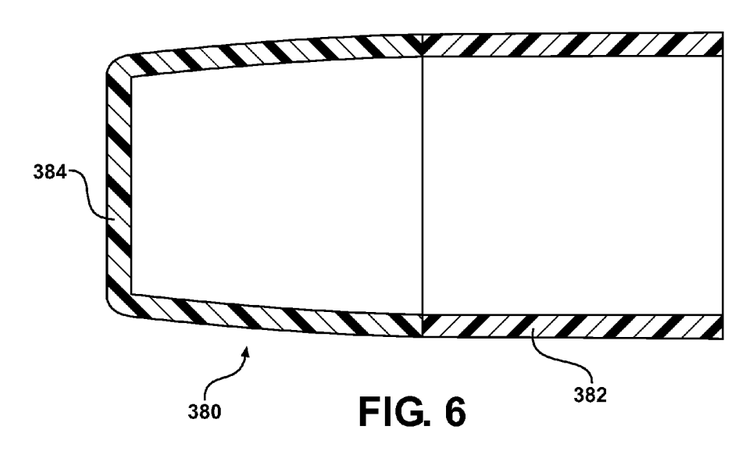
FIG. 6 is a cross sectional view of another part of the embodiment of the cap assembly in FIG. 5.

In accordance with another embodiment of the invention, a cap assembly for a lancing device is illustrated in FIGS. 5A-B and 6. The cap assembly 300 is for use with a lancing device having a housing 305 and a lancet firing mechanism disposed therein, and a lancet 307, one example being that described in the overview. The cap assembly 300 comprises a first cap 310 shown in FIG. 5A and a second cap 350 shown in FIG. 5B. The first cap 310 comprises a skin-engaging end 312 defining a piercing aperture 314, an end 316 opposite the skin-engaging end 312 configured to removably attach to the housing 305, and a lancet receiver 318 configured to receive the lancet 307 through the piercing aperture 314. The second cap 350 comprises a skin-engaging end 352 defining a peripheral skin engaging surface 354, an end 356 opposite the skin-engaging end 352 and configured to removably attach to the housing 305, and a lancet receiver 358 configured to receive the lancet 307 and positioned within the second cap 350 such that an end 360 of the lancet receiver 358 is circumscribed by and is substantially co-planar with the peripheral skin engaging surface 354, the lancet receiver end 360 defining the piercing aperture 362.

In other words, the first cap 310 is configured for AST mode, and the second cap is configured for finger mode. The AST and finger modes and the positioning of the lancet receiver with each mode are described in detail above and are equally relevant to this embodiment. The user selects a cap 310, 350 depending on the tissue site the user is going to lance.

The lancet receiver 318, 358 is fixedly engaged within its respective cap 310, 350. Alternatively, the lancet receiver 318, 358 can be integral with its respective cap 310, 350, for example, formed from the same mold. The lancet receiver 318, 358 has the same geometry in each cap 310, 350 such that the same lancet 307 or type of lancet 310 can be used with either cap 310, 350. The lancet receiver 318, 358 of each cap releasably engages the lancet or the lancet sleeve if the lancet is of such a type. The lancet receiver 318, 358 is generally tubular in construction with a receiver body defining an elongated inner chamber 320, 364 therein that is sized and configured to receive a lancet 307 such as the one shown in FIG. 2. For example, the diameter of the lancet receiver can range from 3 mm to less than 6 mm. The elongated interior chamber 320, 364 is configured for mating engagement with the external contours of the lancet 307 and/or lancet sleeve.

The lancet 307, when in the lancet receiver 318, 358 of either cap 310, 350, engages the lancet firing mechanism within the housing 305. The lancet 307 is fixed in relation to the housing 305 when the lancet 307 has engaged the lancet firing mechanism.

Each cap 310, 350 is configured to selectively adjust a depth of penetration of the lancet 307 via movement of the cap 310, 350 along the caps' central axis relative to the housing 305. With the lancet 307 fixed in relation to the housing 305, the depth to which the lancet 307 will penetrate the skin can be adjusted by moving the selected cap 310, 350 away from and toward the housing 305 along the central axis. This penetration depth adjustment can be performed in both the finger mode and the AST mode, as it can be performed with each cap of the cap assembly. The relationship between cap position and penetration depth of the lancet is described above.

Selective adjustment of the penetration depth can be accomplished via rotation of the removably attached cap with respect to the housing 305. The end 316, 356 of the selected cap 310, 350 opposite the skin-engaging end 312, 352 can be threaded, with the corresponding end of the housing 305 also threaded, as shown in FIGS. 5A and B. The penetration depth can be adjusted by rotating the attached cap 310, 350, thereby moving the cap away from and towards the housing 305 as desired or required.

The motion of depth adjustment along the axis A can be limited by the length of the threads, cam or other adjustment means, or, alternatively, stops can be incorporated to limit the length of movement. The threaded cap is an example and is not meant to be limiting. The caps can be moved in any way known by those skilled in the art. For example, the caps and housing can snap together at different depths, wherein squeezing the selected cap provides clearance to move between depths. The caps can be moved with a cam trail and a cam follower. An intermediate member can be used between the cap and the housing with the cam trail and follower, or can be used in a telescoping manner. The caps can friction fit the housing and be pulled or pushed along the axis.

The cap assembly 300 can further comprise a storage cap 380, as shown in FIG. 6. The storage cap 380 can have the same overall shape of the first and second caps 310, 350 such that it is removably attached to the housing. The storage cap 380 has a body 382 and a closed end 384 so that when attached to the housing, the interior of the lancing device is kept free from dirt and debris.

It is also contemplated that the cap assembly 300 may comprise additional caps as desired or required. For example, caps with different sized apertures may be provided. Caps of different lengths may be provided to change the penetration depth rather than movement of the cap along the axis. Caps of different colors, opacity and transparency can be provided. Caps with different shaped apertures can be provided. Caps for particular lancet designs can be provided.

It is further contemplated that the cap assembly 300 may come with a storage device, such as a bag or a box, in which to store the cap or caps that are not currently in use. This could be used to keep the caps clean and free of dirt and debris, as well as prevent loss of a cap.

Figure 7:
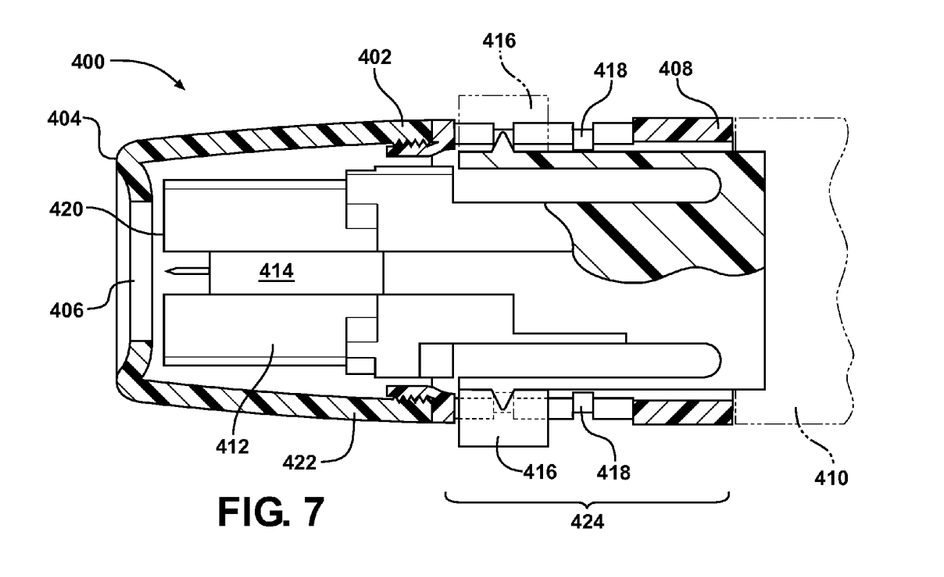
FIG. 7 is a cross sectional view of yet another embodiment of a cap as disclosed herein and shown in finger mode.

Yet another embodiment of a cap for a lancing device is described with reference to FIGS. 7 and 8. The cap 400 with adjustable modes can be used with a lancing device having a housing, for example, as illustrated in FIG. 1. The cap 400 comprises a cap body 402 with a skin-engaging end 404 defining a piercing aperture 406, an end 408 opposite the skin-engaging end 404 configured to removably attach to the housing 410, and a lancet receiver 412 movably attached within the cap body 402 and configured to receive a lancet 414. The lancet receiver 412 has at least one protrusion 416, shown here with two, extending through corresponding opening(s) 418 in the cap body 402 wherein movement of the protrusions 416 move the lancet receiver 412 between a forward position in which an end 420 of the lancet receiver 412 is interposed in the piercing aperture 406 (shown in FIG. 7) and a rearward position distanced from the skin-engaging end 404 of the cap body 402 (shown in FIG. 8).

The cap 400 is in finger mode, described in detail above, when the end 420 of the lancet receiver 412 is interposed in the piercing aperture 406. In finger mode, the end 420 of the lancet receiver 412 can be substantially coplanar with the skin-engaging end 404. In other words, when the lancet receiver 412 is interposed within the piercing aperture 406, it adjusts the effective size of the piercing aperture 406 to that of the smaller diameter of the end 420 of the lancet receiver 412, as shown in FIG. 7.

Figure 8:
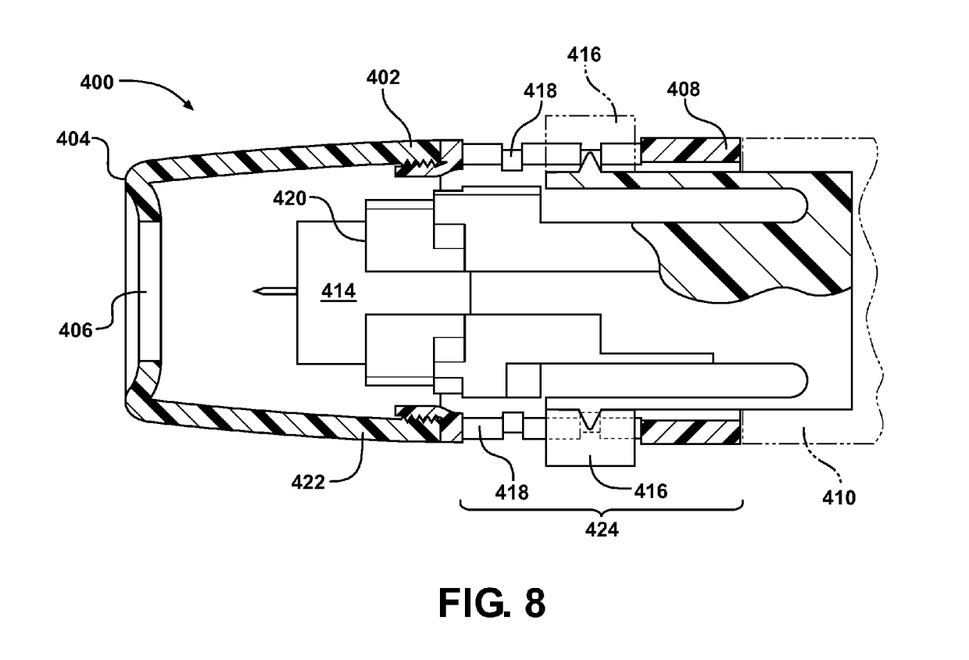
FIG. 8 is a cross sectional view of the embodiment of the cap shown in FIG. 7 but in AST mode.

The cap 400 is in AST mode, also described in detail above, when the lancet receiver 412 is withdrawn from the piercing aperture 406, as illustrated in FIG. 8. The lancet receiver 412 in this position adjusts the effective size of the piercing aperture 406 to a larger diameter corresponding to the diameter of unobstructed piercing aperture 406. This larger diameter is sufficiently large to allow the user's skin to pucker into the piercing aperture 406.

The mode change between finger and AST is accomplished by axial movement of the lancet receiver 412 between the two positions. In this embodiment, the protrusions 416 extending from the lancet receiver 412 and through the openings 418 in the cap body 402 are squeezed together to unlock the lancet receiver 412, allowing the lancet receiver 412 to be moved by moving the protrusions 416 from an existing position to the other position. When the protrusions 416 are released, the protrusions 416 lock the lancet receiver 412 into place. It is contemplated that only one protrusion can be used to move the lancet receiver. The protrusion can be an arm or a button, for example. Other means of moving the lancet receiver known to those skilled in the art can be used as desired or required. For non-limiting examples, a cam trail and cam follower can be used, a lever moved in the direction along axis A can be used with a separate locking mechanism, or a button that is pushed in on one side while out on the other can be used.

The lancet 414, when in the lancet receiver 412, engages a lancet firing mechanism (not shown) within the housing 410. The lancet 414 is fixed in relation to the housing 410 when the lancet 414 has engaged the lancet firing mechanism.

The cap 400 is configured to selectively adjust a depth of penetration of the lancet 414 via movement of the cap 400 along the caps' central axis relative to the housing 410. This penetration depth adjustment can be performed in both the finger mode and the AST mode. The relationship between cap position and penetration depth of the lancet is described above.

Selective adjustment of the penetration depth can be accomplished via rotation of the removably attached cap 400 with respect to the housing 410 as described above. Alternatively, the cap body 402 can comprise a proximal member 422 having the skin engaging end 404 and a distal member 424 having the at least one opening 418 and the end 408 opposite the skin-engaging end configured to removably attach to the end of the housing 410. The proximal member 422 and the distal member 424 are threadably engaged as shown in FIGS. 7 and 8. The penetration depth of the lancet 414 is adjusted by rotating the proximal member 422 away from and toward the distal member 424 via the threads. The motion of depth adjustment along the axis A can be limited by the length of the threads or alternatively stops can be incorporated to limit the length of movement if desired or required.

The embodiments of the cap and cap assemblies disclosed herein can be similarly operated with a lancing device and lancet, such as those described with reference to FIGS. 1 and 2. The reference numbers used in the overview will be used in FIGS. 9A-C to represent that any of the caps disclosed can be operated in the manner described below.

Figure 9A:
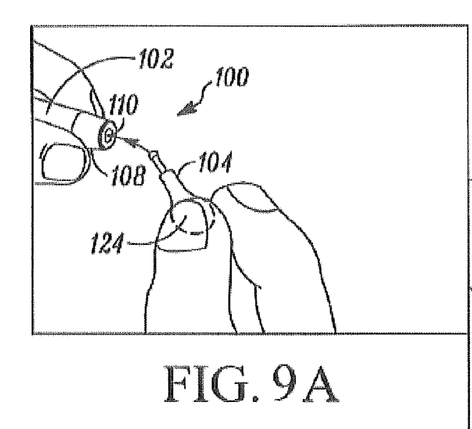
FIGS. 9A through 9C are a series of diagrams showing the general operation of cap assembly embodiments of FIGS. 3-8.
Figure 9B:
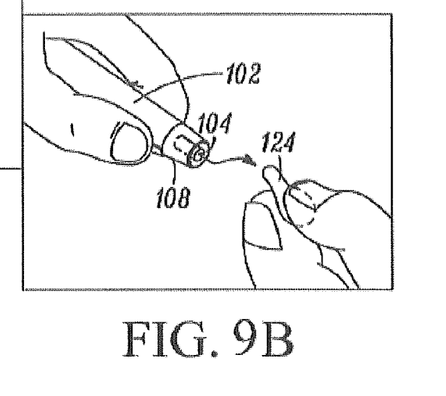

In FIG. 9A, the user inserts lancet 104 into lancing device 102 through piercing aperture 110. Removable tab 124 (shown in FIG. 9A with phantom lines seen through the user's thumb) can provide a convenient finger-grip while also protecting the user from exposure to the sharp tip and maintains the sterility of the sharp tip. Once lancet 104 is fully inserted, removable tab 124 extends from piercing aperture 110. Referring to FIG. 9B, the user then twists the removable tab 124 to sever it from the lancet 104 along the frangible connection and pulls removable tab 124 off of the sharp tip. At this time, the sharp tip is enclosed within cap 108. Once removable tab 124 is removed, substantially all of lancet 104 can be enclosed by cap 108 or cap and housing 106, so that no part of lancet 104 protrudes beyond piercing aperture 110 by an amount sufficient to displace the user's skin from the skin engaging surface of cap 108.

Figure 9C:
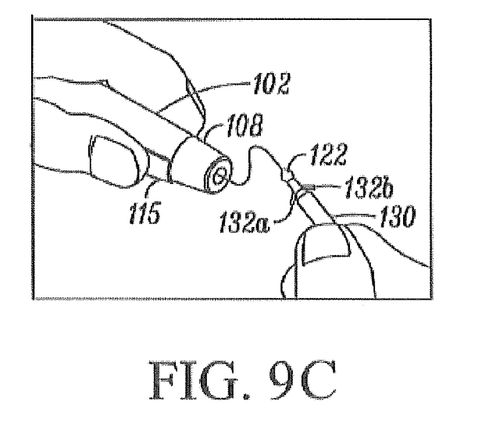

Referring to FIG. 9C, after lancing device 102 is fired, the user can eject lancet 104 through piercing aperture 110 of cap 108. The lancet 104 can be withdrawn from the cap 108 by a user's finger tips. The lancet 104 can also be expelled from lancet device 102 by force of gravity after ejection, without the user having to touch lancet 104.

Although not shown, it is contemplated that any of the embodiments disclosed herein can include indicia on the outer circumferential surface of the cap and/or housing to indicate whether the cap is set to finger mode or AST mode and to indicate the penetration depth setting. For example, indicia can be a diagram of a human body, conveying to the user the fact that in AST mode bodily fluid can be drawn from tissue other than a finger. Lines of varying sizes may indicate the depth setting. Any descriptive symbols or icons may be used as desired or required.

The above-mentioned embodiments have been described in order to allow easy understanding of the present invention. The invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. An adjustable cap assembly for a lancing device having a housing, the assembly comprising:
    a cap comprising:
        a cap body with a skin-engaging end, an opposing end of the skin-engaging end and an outer wall extending therebetween, the skin-engaging end defining an opening;
        a distal member having a forward end directly attached to the opposing end of the cap body, a rearward end opposite the forward end configured to removably engage an end of the housing, and an outer wall extending therebetween such that the outer wall of the cap body, the outer wall of the distal member and the housing are axially aligned to define an interior of the lancing device, wherein the cap body is configured to move axially to adjust a penetration depth of the lancet relative to the distal member and the housing;
    a lancet receiver within the cap configured to receive a lancet, and movable between a forward position and a rearward position; and
    a piercing aperture through which a tip of the lancet extends during lancing, wherein the piercing aperture is defined by the lancet receiver when the lancet receiver is in the forward position and defined by only the opening when the lancet receiver is in the rearward position; wherein the lancet receiver is configured with at least one protrusion extending through a corresponding opening in the distal member of the cap, wherein movement of the at least one protrusion moves the lancet receiver between the forward position in which an end of the lancet receiver is interposed in the opening, thereby effectively reducing the size of the opening, and a rearward position in which the end of the lancet receiver is distanced from the skin-engaging end of the cap body.

2. The adjustable cap assembly of claim 1, wherein the lancet receiver in the rearward position is sufficiently distanced from the opening to permit skin to pucker through the opening during lancing.

3. The adjustable cap assembly of claim 1, wherein the opposing end of the cap body is configured to threadably attach to the distal member such that the cap body is configured to rotatably adjust the penetration depth of the lancet.

4. The adjustable cap assembly of claim 1, wherein the lancet receiver moves between the forward position and rearward position while the lancet remains stationary relative to the housing.

5. The adjustable cap assembly of claim 1, wherein the lancet receiver is sized to permit insertion of the lancet therethrough while sufficiently narrow to prevent puckering of skin.

6. The adjustable cap assembly of claim 5, wherein a diameter of the lancet receiver ranges from three millimeters or greater to less than six millimeters.

7. The adjustable cap assembly of claim 1, wherein the lancet is configured to engage a lancet firing mechanism within the housing when the lancet is received by the lancet receiver, the lancet configured in fixed relation to the housing when the lancet engages the lancet firing mechanism.

8. The adjustable cap assembly of claim 1, wherein the at least one protrusion comprises two arms extending through opposite openings in the cap body, the arms configured to release the lancet receiver for movement when squeezed and prevent movement of the lancet receiver when released, wherein the lancet does not move with the lancet receiver.

* * * * *